(12) United States Patent  (10) Patent No.: US 8,382,710 B2
Filippi  (45) Date of Patent: Feb. 26, 2013

(54) SYRINGE

(75) Inventor: Filippo Filippi, London (GB)

(73) Assignee: Sperian Securities Inc., Panama (PA)

( * ) Notice: Subject to any disclaimer, the term of this patent is extended or adjusted under 35 U.S.C. 154(b) by 505 days.

(21) Appl. No.: 11/663,015

(22) PCT Filed: Sep. 15, 2005

(86) PCT No.: PCT/EP2005/009944
§ 371 (c)(1),
(2), (4) Date: Apr. 15, 2008

(87) PCT Pub. No.: WO2006/029873
PCT Pub. Date: Mar. 23, 2006

(65) Prior Publication Data
US 2008/0287882 A1   Nov. 20, 2008

(30) Foreign Application Priority Data

Sep. 16, 2004 (GB) .................................. 0420640.5

(51) Int. Cl.
*A61M 5/00* (2006.01)

(52) U.S. Cl. ......... 604/110; 604/192; 604/195; 604/196

(58) Field of Classification Search .................. 604/110, 604/195, 196
See application file for complete search history.

(56) References Cited

U.S. PATENT DOCUMENTS

| 5,017,187 | A | * | 5/1991 | Sullivan | 604/110 |
| 5,211,628 | A | | 5/1993 | Marshall | |
| 6,706,019 | B1 | | 3/2004 | Parker et al. | |
| 6,712,788 | B2 | * | 3/2004 | Righi et al. | 604/110 |
| 2003/0163092 | A1 | | 8/2003 | Parker et al. | |
| 2003/0208164 | A1 | * | 11/2003 | Botich et al. | 604/195 |
| 2004/0054324 | A1 | * | 3/2004 | Montalvo et al. | 604/110 |

FOREIGN PATENT DOCUMENTS

| DE | 43 14 395 C1 | 12/1994 |
| DE | 195 28 091 A1 | 2/1997 |
| EP | 1 273 316 A1 | 1/2003 |
| WO | WO 03/051436 A2 | 6/2003 |

* cited by examiner

*Primary Examiner* — Kevin C Sirmons
*Assistant Examiner* — Brandy C Scott
(74) *Attorney, Agent, or Firm* — Blakely, Sokoloff, Taylor & Zafman

(57) ABSTRACT

A syringe (1) comprises a barrel (2) for containing a substance to be injected, a needle carrier (12) for carrying a needle (10), and a plunger (3) which is adapted to be movable in the barrel 2 to expel the substance to be injected from the needle (10). The plunger (3) has a first part (3*a*), a second part (3*b*) and a resilient member (6) therebetween, the first (3*a*) and second (3*b*) parts being adapted to be releasably locked together to hold the resilient member (6) in a compressed state. In use, the first part 3*a* of the plunger (3) and the needle carrier (12) are adapted to engage one another following expulsion of the substance, and the second part (3*b*) of the plunger (3) is adapted to be unlocked from the first part (3*a*) following said engagement, allowing the resilient member (6) to expand to propel the needle carrier (12) into the barrel (2).

13 Claims, 10 Drawing Sheets

Figure 11

SYRINGE

This is a non-provisional application claiming the benefit of International application number PCT/EP2005/009944 filed Sep. 15, 2005.

FIELD OF THE INVENTION

The present invention relates to a syringe, and in particular, to a safety syringe.

BACKGROUND

Safety syringes are used in healthcare to prevent needle-stick injuries, that is, injuries to health workers and other persons that result from being stabbed by needles that have been used to inject patients. In many cases, needlestick injuries are minor, but in cases where the needle concerned is infected, for example, with the AIDS virus, the injuries can have serious implications.

A further concern relating to the use of needles in the healthcare field is re-use. In order to prevent the spread of disease, sharing of needles should be prevented.

One way of preventing needlestick injuries and re-use of needles is to ensure that needles are unusable following use.

An example of a safety syringe that prevents re-use of the syringe needle is disclosed in EP 0 636 381B. That syringe provides for engagement of a needle hub, which carries a needle, by a plunger that is used to expel a substance from the syringe, following the expulsion of that substance. Once the plunger has engaged the needle hub, it can be manually retracted into the syringe, bringing the needle hub and attached needle with it. A stop is located in the syringe to prevent removal of the plunger from the syringe, so that the needle hub and needle remain inside the main body of the syringe, so as to avoid injury.

One disadvantage of the syringe disclosed in EP 0 636 381B is that the plunger and attached needle hub need to be retracted into the syringe by the healthcare worker, which means that human error could result in the needle hub not being retracted at all, for example, because the healthcare worker omitted to complete the retraction step. For this reason, automatic retraction of the needle hub into the syringe is desirable.

An automatic retraction system for syringes is described in U.S. Pat. No. 6,572,584. That system incorporates a pre-stressed compression spring in the region of the needle hub. When the compression spring is allowed to relax following injection of the substance carried by the syringe, the needle hub is forced into the syringe by the restoring force of the spring, so that the needle is safely disposed of. Although the spring in the region of the needle hub is effective in automatically retracting the needle hub into the syringe, the syringe has a complex construction, which means that it is costly to produce.

SUMMARY OF THE INVENTION

It is an aim of the present invention to ameliorate at least some of the disadvantages of the prior art discussed above.

In a first aspect, the present invention provides a syringe comprising a barrel for containing a substance to be injected, a needle carrier for carrying a needle, and a plunger which is adapted to be movable in the barrel to expel the substance to be injected through the needle, the plunger having a first part, a second part and a resilient member therebetween, the first and second parts being adapted to be releasably locked together to hold the resilient member in a compressed state, wherein, in use, the first part of the plunger and the needle carrier are adapted to engage one another following expulsion of the substance, and the second part of the plunger is adapted to be unlocked from the first part following said engagement, allowing the resilient member to expand to propel the needle carrier into the barrel.

The expansion of the resilient member within the plunger assembly following its storage in a compressed state provides an effective means of withdrawing the needle into the barrel of the syringe so that it cannot cause injury, yet the construction of the syringe is not complex. The retraction of the needle also does not require a manual input in addition to actuation of the plunger, and is thus automatic, which means that the risk of the needle not being retracted following use is low. A health worker using the syringe does not need to consciously withdraw the needle.

Furthermore, the location of the resilient member within the plunger means that it does not contact the substance within the barrel, thus avoiding contamination of that substance. In addition, the syringe is relatively easy to assemble, which reduces production costs.

In a preferred embodiment of the invention, the first part of the plunger is adapted to engage the needle carrier by virtue of engagement means. The engagement means preferably comprise a receptacle in the first part of the plunger that is adapted to engage a resilient prong on the needle carrier. In a preferred embodiment, the resilient prong on the needle carrier is located entirely within a needle hub that is attachable to the barrel of the syringe. This protects the needle carrier, and in particular the prong, when it is not in use, and when the needle hub is being attached to the barrel of the syringe. In addition, it avoids interaction of the resilient prong with the substance in the syringe barrel, which could otherwise result in the introduction of air bubbles to the substance. Rather than, or in addition to the prong being resilient, the receptacle may be made of a resilient material. The prong could be on the first part of the plunger and the receptacle could be on the needle carrier.

Alternative engagement means comprise a socket in the needle carrier and a corresponding ball on the first part of the plunger. The socket, or more preferably the ball, has sufficient resilience to allow these parts to engage and lock together. These engagement means are structurally uncomplicated, which results in simplified manufacture and operation of the syringe.

Preferably, the first and second parts of the plunger are adapted to be releasably locked together by virtue of locking means. The locking means preferably comprise a protrusion on the second part of the plunger that is adapted to engage a corresponding recess on the first part, or vice versa. Again, this construction is relatively uncomplicated, which facilitates manufacture and operation of the syringe.

The plunger is preferably adapted to be irremovably contained in the barrel of the syringe following retraction of the needle hub. This avoids the possibility of tampering with the plunger to attempt to remove the needle from its retracted position within the barrel.

In a preferred embodiment of the invention, the first part of the plunger is arranged inside the second part of the plunger. This arrangement has the advantage of being space-efficient.

In a second aspect, the present invention provides a syringe comprising a barrel for containing a substance to be injected, and receiving a needle carrier for carrying a needle, and a plunger which is adapted to be movable in the barrel to expel the substance to be injected through the needle, the plunger having a first part, a second part and a resilient member therebetween, the first and second parts being adapted to be releasably locked together to hold the resilient member in a compressed state, wherein, in use, the first part of the plunger is adapted to engage the needle carrier following expulsion of the substance, and the second part of the plunger is adapted to be unlocked from the first part following said engagement allowing the resilient member to expand to propel the needle carrier into the barrel.

In a third aspect, the invention provides a plunger for a syringe that is adapted to be movable in the syringe to expel a substance from the syringe, the plunger comprising a first part and a second part and a resilient member therebetween, the first and second parts being adapted to be releasably locked together to hold the resilient member in a compressed state, wherein the plunger is adapted to engage a needle carrier of the syringe following expulsion of the substance from the syringe, and the second part of the plunger is adapted to be unlocked from the first part following said engagement, allowing the resilient member to expand to propel the needle carrier into a barrel of the syringe.

In a fourth aspect, the present invention provides a method of retracting a needle into a barrel of a syringe, to which it is attached, following use, comprising compressing a resilient member between two parts of a plunger and locking those parts together to retain compression; attaching one part of the plunger to a needle carrier holding the needle in the syringe; and unlocking the two parts of the plunger so that the compressed resilient member relaxes and the relaxation causes the first part of the plunger and the needle carrier to which it is attached, to be retracted into the barrel.

BRIEF DESCRIPTION OF THE DRAWINGS

Embodiments of the invention will be described, by way of example, with reference to the following drawings, in which.

DESCRIPTION OF AN EMBODIMENT

The invention described below is a safety syringe that provides for retraction of a needle attached to the syringe into a barrel of the syringe following use, in order to avoid needle-stick injuries and/or re-use of the needle. The needle is retracted into the barrel of syringe under the action of a spring which is stored in a compressed state in the plunger while the needle is in use.

The needle is held by a needle carrier with which the plunger engages at the end of its stroke. When the plunger reaches the end of its stroke it also releases the spring from its compressed state so that its expansion causes the needle carrier and needle to be retracted into the barrel of the syringe.

Figures 1, 2:
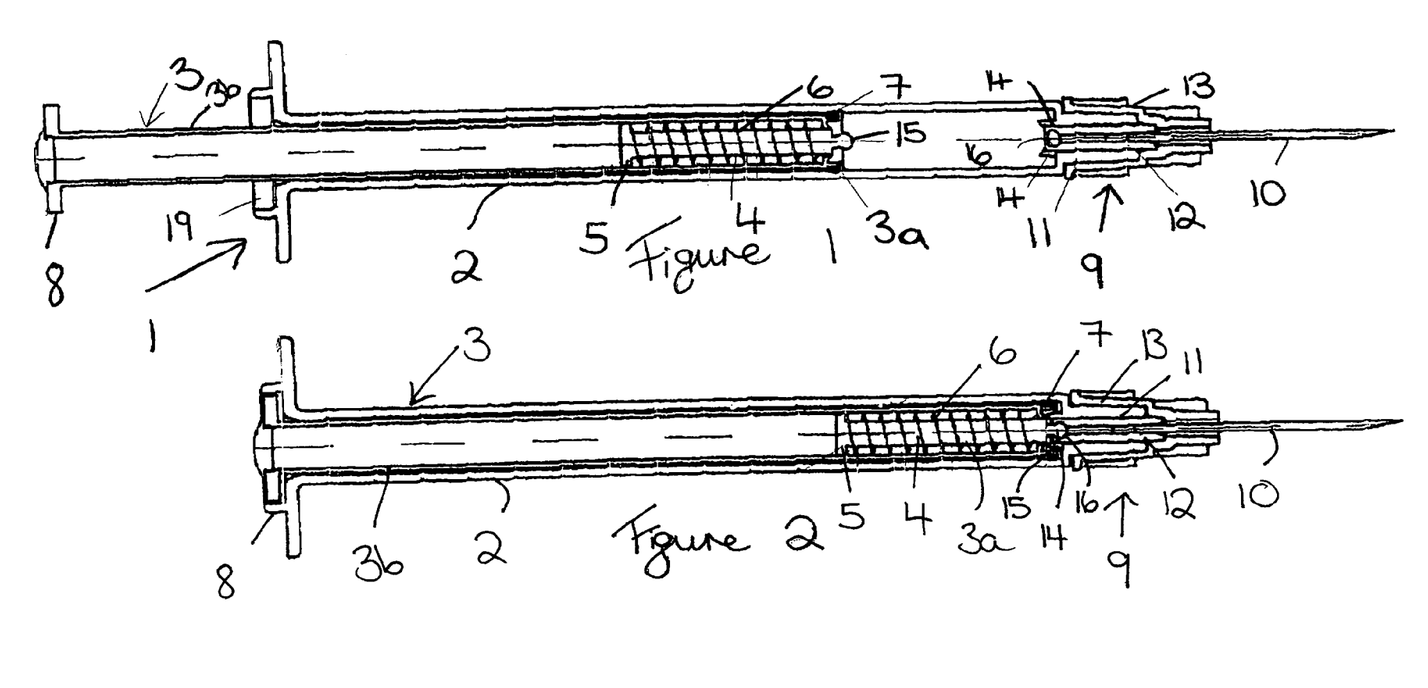
FIG. 1 shows a side view of a syringe in accordance with a first embodiment of the present invention in a first position.
FIG. 2 shows a side view of a syringe in accordance with a first embodiment of the present invention in a second position.

In FIG. 1, a syringe 1 has a hollow elongate barrel 2 for containing a substance, such as a medicament, to be injected and an elongate plunger 3 that is movable in the barrel 2 for dispensing the substance. The plunger 3 has a first part 3a and a second part 3b, the first part 3a being located within the second part 3b, which is hollow, so that the first part 3a is movable within the second part 3b. The first part 3a is an elongate tubular member 4 with an integral head 5 of a diameter that is greater than that of the elongate tubular member 4 and substantially the same as the inner diameter of the second part 3b, although there is play between the head 5 and the inner surface of the second part 3b, so that the head 5 does not restrict movement of the first part 3a within the second part 3b. The first part 3a carries a resilient member in the form of a spring 6, and the second part 3b has a seal 7 that surrounds its distal end. The seal 7 prevents the introduction of air and other contaminants into the substance. An actuator 8 for moving the plunger 3 within the barrel 2 is at a proximal end of the second part 3b of the plunger. The plunger 3 has vents (not shown) that avoid the build-up of excessive pressure in the plunger 3.

The syringe 1 has a needle hub 9 at its distal end, in which a needle 10 is arranged in such a way that it protrudes from the end of the barrel 2 so that it is easily accessible for injecting purposes.

The needle hub 9 is positioned in and around a collar 11 at a distal end of the barrel 2. An inner part or needle carrier 12, to which the needle 10 is bonded, of the needle hub 9 is located inside the collar 11, and an outer part 13 of the needle hub 9, which has a Luer taper, surrounds the collar 11. The outer part 13 has a standard length of engagement. The needle hub 9 is retained in position on the collar 11 by means of a close fit. There are also retaining means 14 in the form of three resilient projections inside the barrel 2 which are spaced equally around the circumference of the needle carrier 12 and grip the needle carrier 12 to prevent its axial movement.

The first part 3a of the plunger 3 has plunger engagement means 15 in the form of a resiliently deformable ball that protrudes from the distal end of the part 3a. The plunger engagement means 15 correspond to carrier engagement means 16 in the form of a socket on the needle carrier 12 of the needle hub 9.

Figure 6:
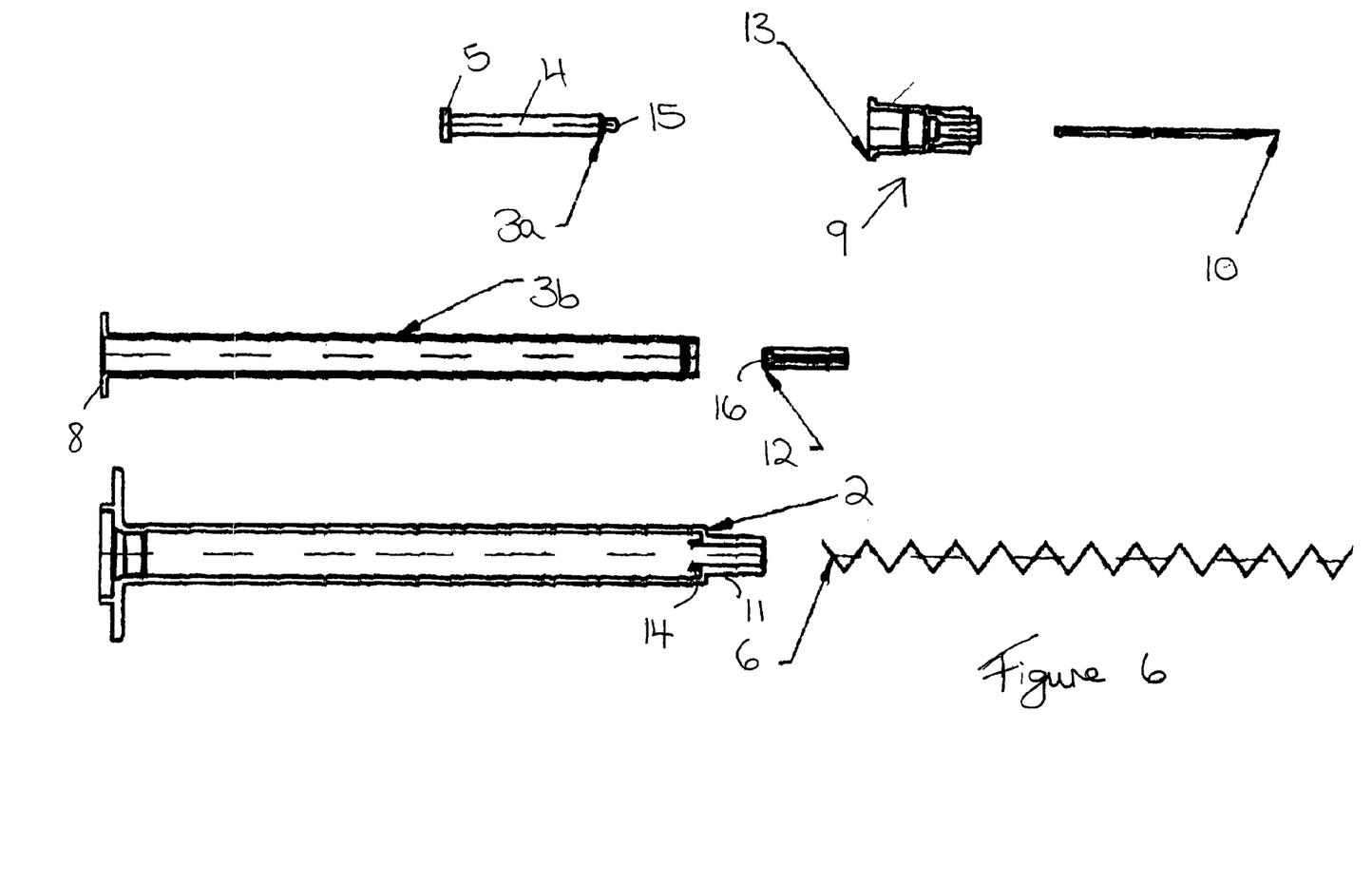
FIG. 6 shows an exploded side view of the syringe of FIGS. 1 to 5.
Figure 7:
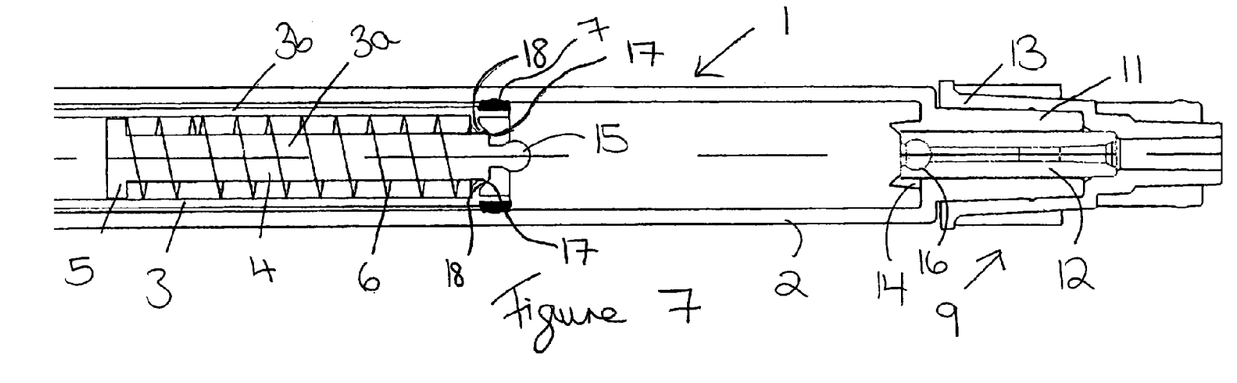
FIG. 7 shows a side view of a section of the syringe in the position shown in FIG. 1.

The first part 3a of the plunger 3 additionally has first locking means 17 in the form of a curved recess (see FIG. 6), which engages corresponding second locking means 18 in the form of projections with a curved surface on the second part 3b of the plunger 3.

In use, the needle hub 9 is initially removed from the distal end of the syringe 1 prior to use to allow attachment of a suction needle (not shown) for introducing the substance to be injected into the syringe 1. Once the syringe 1 has been filled with the substance, the needle hub 9 is placed on the syringe 1 by push-fitting it onto the end of the barrel 2. The collar 11 on the barrel serves to guide the needle hub 9 onto the barrel 2 so that it can be fitted easily.

To inject the substance in the syringe 1 into a patient, the needle 10 is inserted, e.g. in the patient's skin, and a force is applied to the actuator 8 on the plunger 3 to cause the plunger 3 to move in the barrel 2. As the plunger 3 moves through the barrel 2, the substance is expelled through the needle 10 into the patient.

When an appropriate dose of the substance has been administered, the plunger 3 will have moved a considerable way along the barrel 2, but there will be a small clearance between the end of the plunger 3 and the end of the barrel 2. By continuing to apply a force to the actuator 8, the ball 15 on the first part 3a of the plunger 3b will engage the needle carrier 12 by deforming to fit into the socket 16 in the needle carrier 12.

Figure 8:
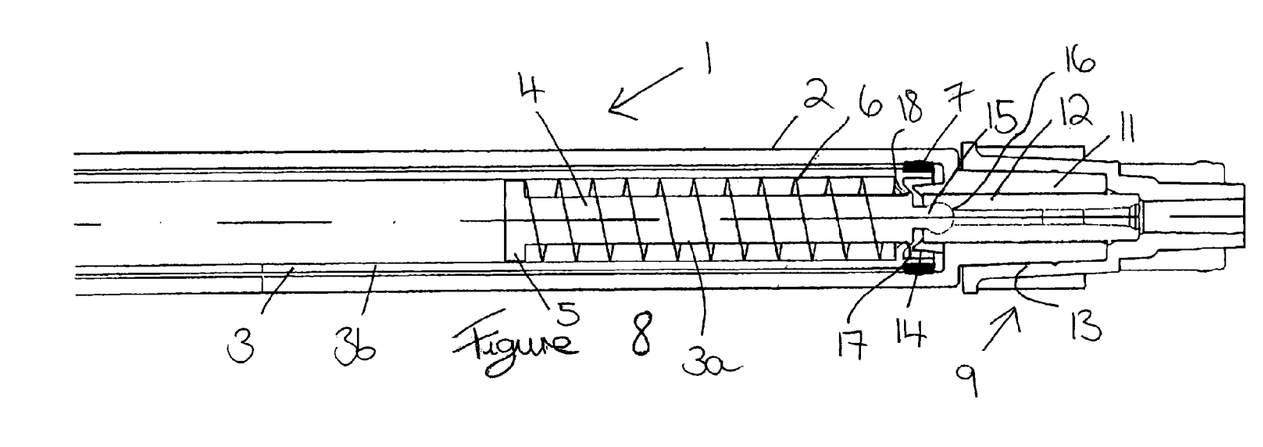
FIG. 8 shows a side view of a section of the syringe in the position shown in FIG. 2.

Once the ball 15 has been located in the socket 16, it will expand so that it is held securely therein. FIGS. 2 and 8 show the location of the plunger 3 following engagement of the ball 15 and socket 16. It can be seen that a clearance remains between the end of the plunger 3 and the end of the barrel 2 when the ball 15 and socket 16 have been engaged.

Figure 3:
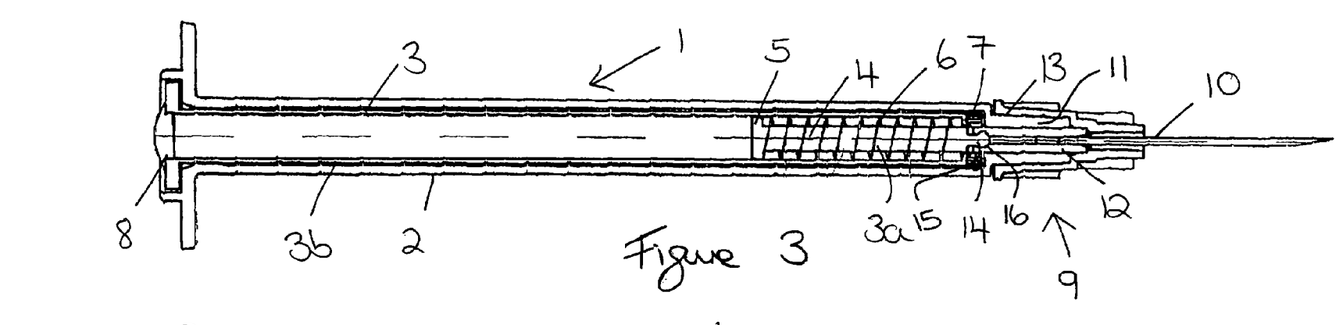
FIG. 3 shows a side view of a syringe in accordance with a first embodiment of the present invention in a third position.
Figure 4:
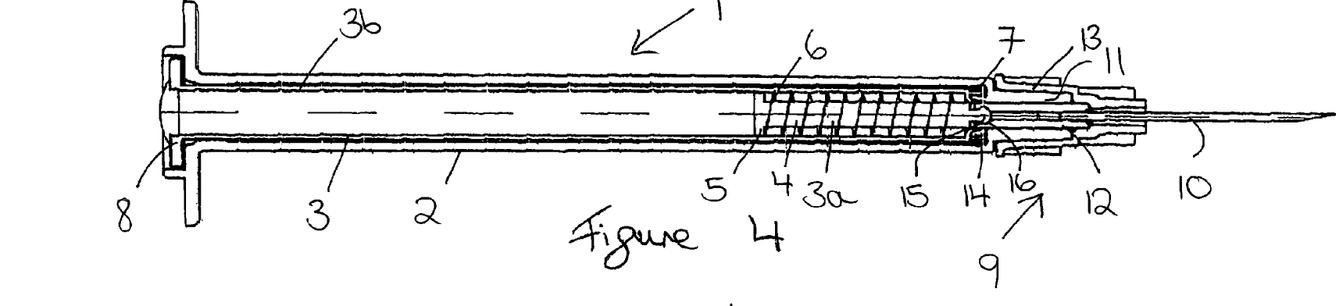
FIG. 4 shows a side view of a syringe in accordance with a first embodiment of the present invention in a fourth position.
Figure 9:
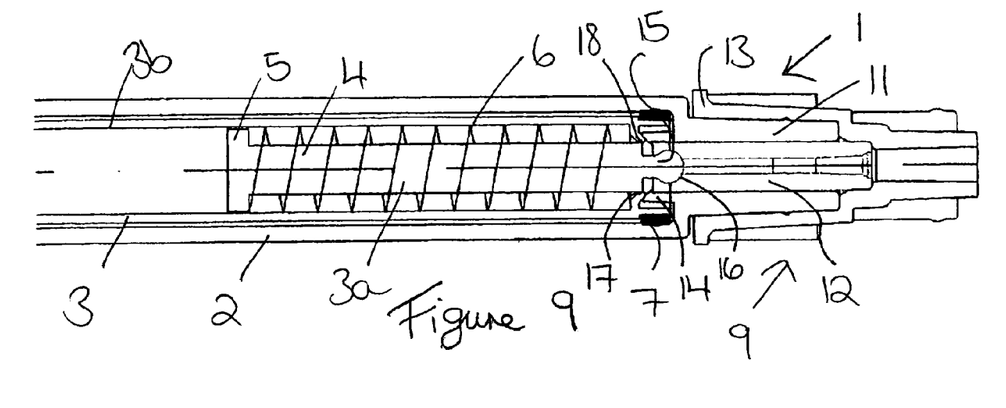
FIG. 9 shows a side view of a section of the syringe in the position shown in FIG. 3.
Figure 10:
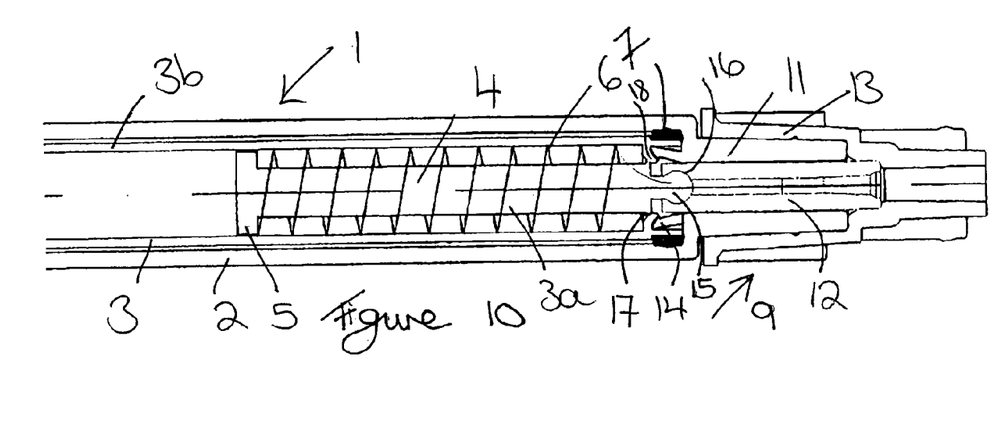
FIG. 10 shows a side view of a section of the syringe in the position shown in FIG. 4.

By continuing to apply a force to the actuator 8, the second part 3b of the plunger 3 is forced to move further along the barrel 3 until the end of the plunger 3 touches the end of the barrel 2, as shown in FIGS. 3 and 9. Since the first part 3a of the plunger 3 cannot move any further at that point due to its attachment with the needle carrier 12, the projections 18 on the second part 3b of the plunger 3b travel along the surface of the recess 17 in the manner of a cam, so that they become free of the recess 17. The projections 18 then move along the resilient projections 14 on the barrel 2 that hold the needle carrier 12 in place inside the barrel, in a similar manner, forcing the resilient projections 14 away from the needle carrier 12 so that it is no longer secured inside the collar 11 (see FIGS. 4 and 10).

The unlocking of the first part 3a and second part 3b of the plunger 3 from one another allows the spring 6 that is carried by the first part 3a of the plunger 3 to expand. Since the first part 3a is now attached to the needle carrier 12 and the needle carrier 12 is no longer gripped in the collar 11 by the resilient projections 14, the needle carrier 12 travels through the barrel 2 under the restoring force of the spring 6 in the direction of the actuator 8.

Figure 5:
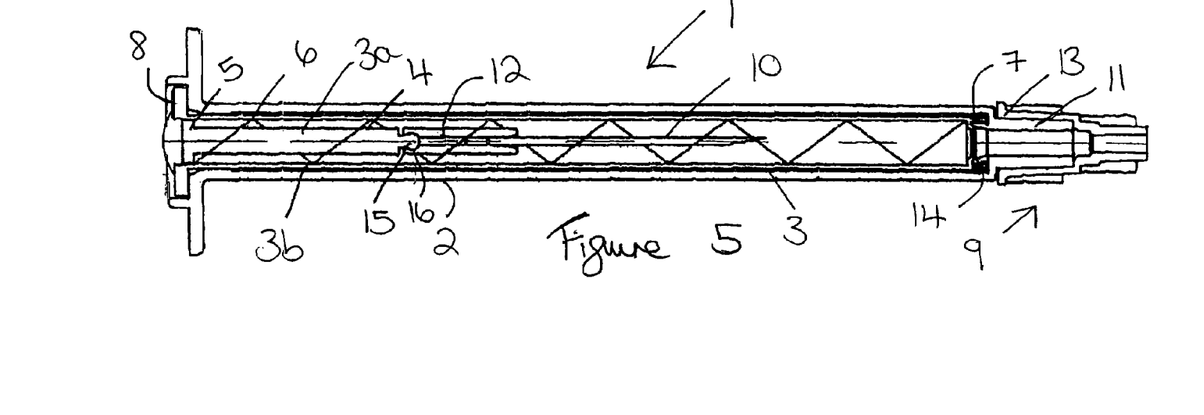
FIG. 5 shows a side view of a syringe in accordance with a first embodiment of the present invention in a fifth position.
Figure 11:
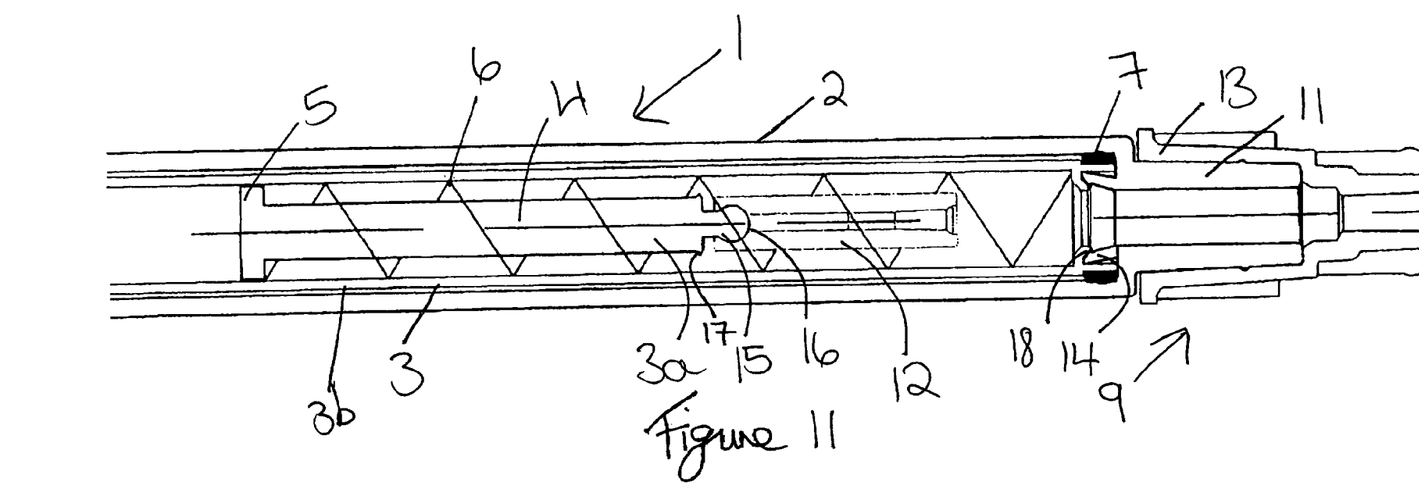
FIG. 11 shows a side view of a section of the syringe in the position shown in FIG. 5.
Figure 12:
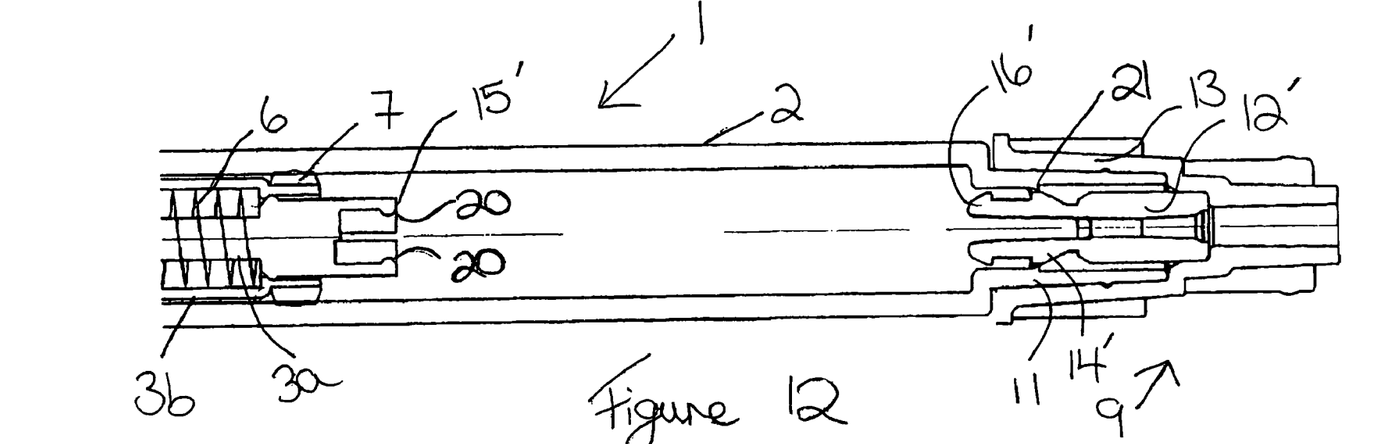
FIG. 12 shows a side view of a section of a syringe in accordance with a second embodiment of the present invention in a first position.
Figure 13:
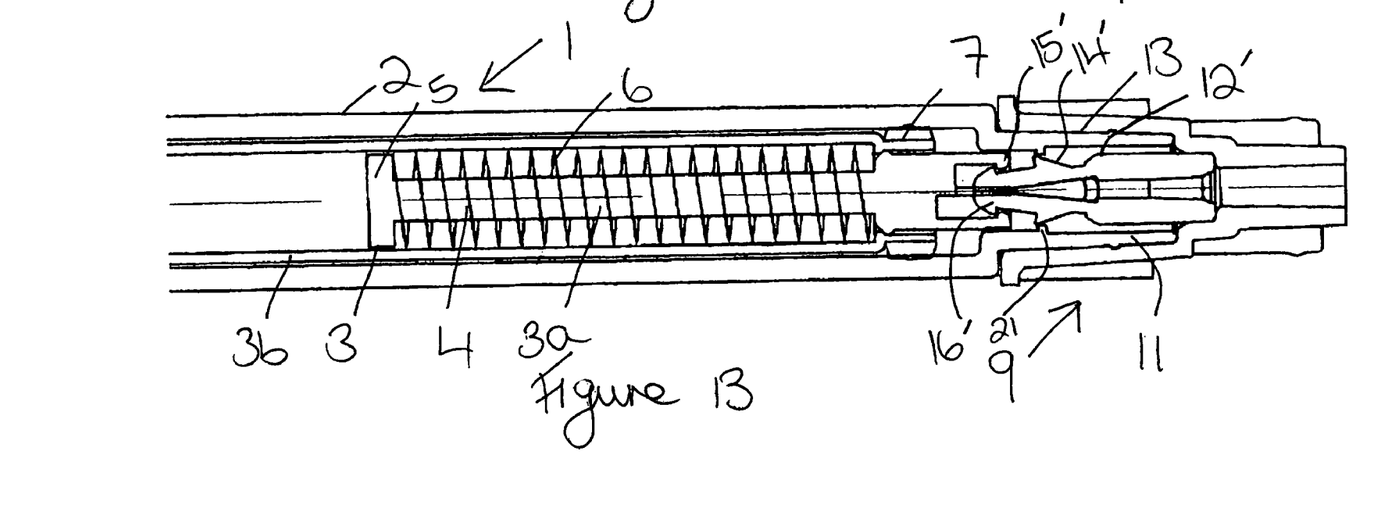
FIG. 13 shows a side view of a section of a syringe in accordance with a second embodiment of the present invention in a second position.
Figure 14:
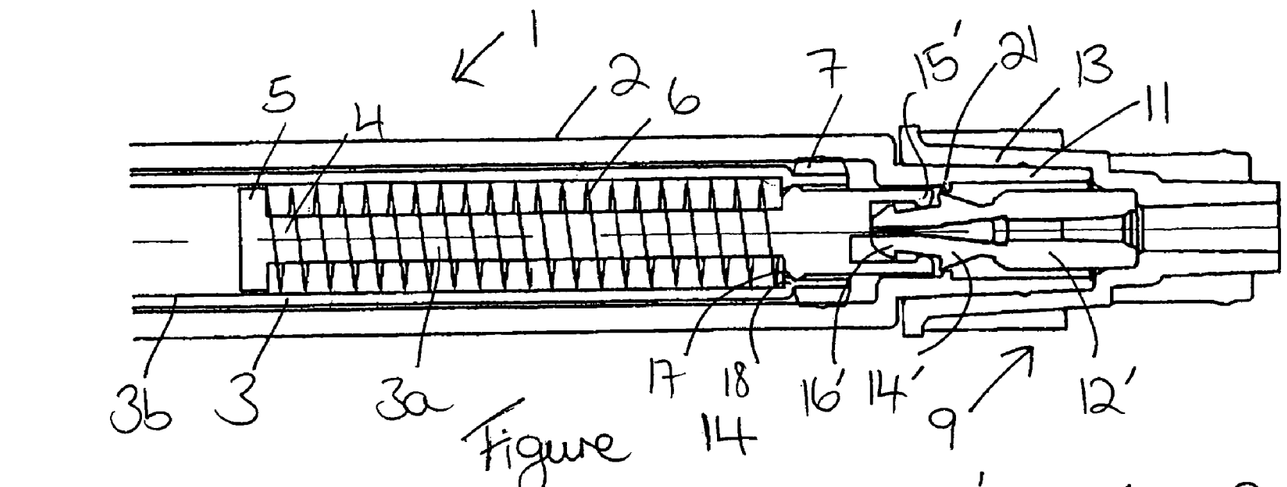
FIG. 14 shows a side view of a section of a syringe in accordance with a second embodiment of the present invention in a third position.
Figure 15:
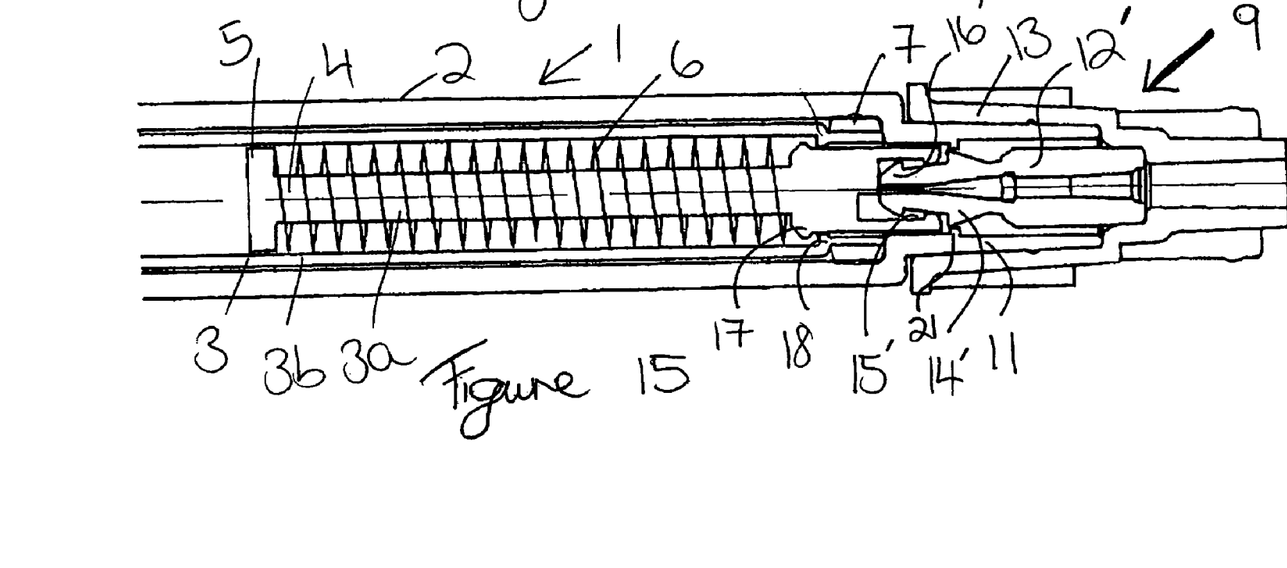
FIG. 15 shows a side view of a section of a syringe in accordance with a second embodiment of the present invention in a fourth position.
Figure 16:
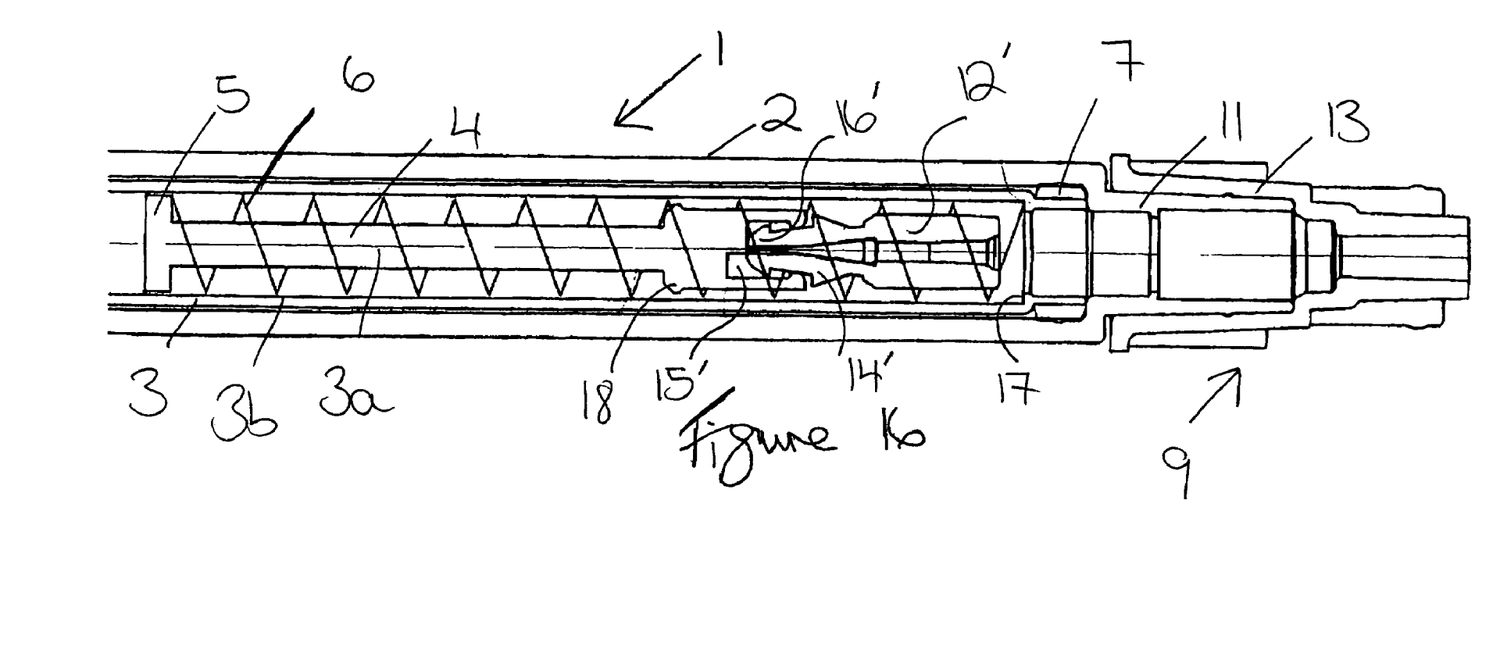
FIG. 16 shows a side view of a section of a syringe in accordance with a second embodiment of the present invention in a fifth position.
Figure 17:
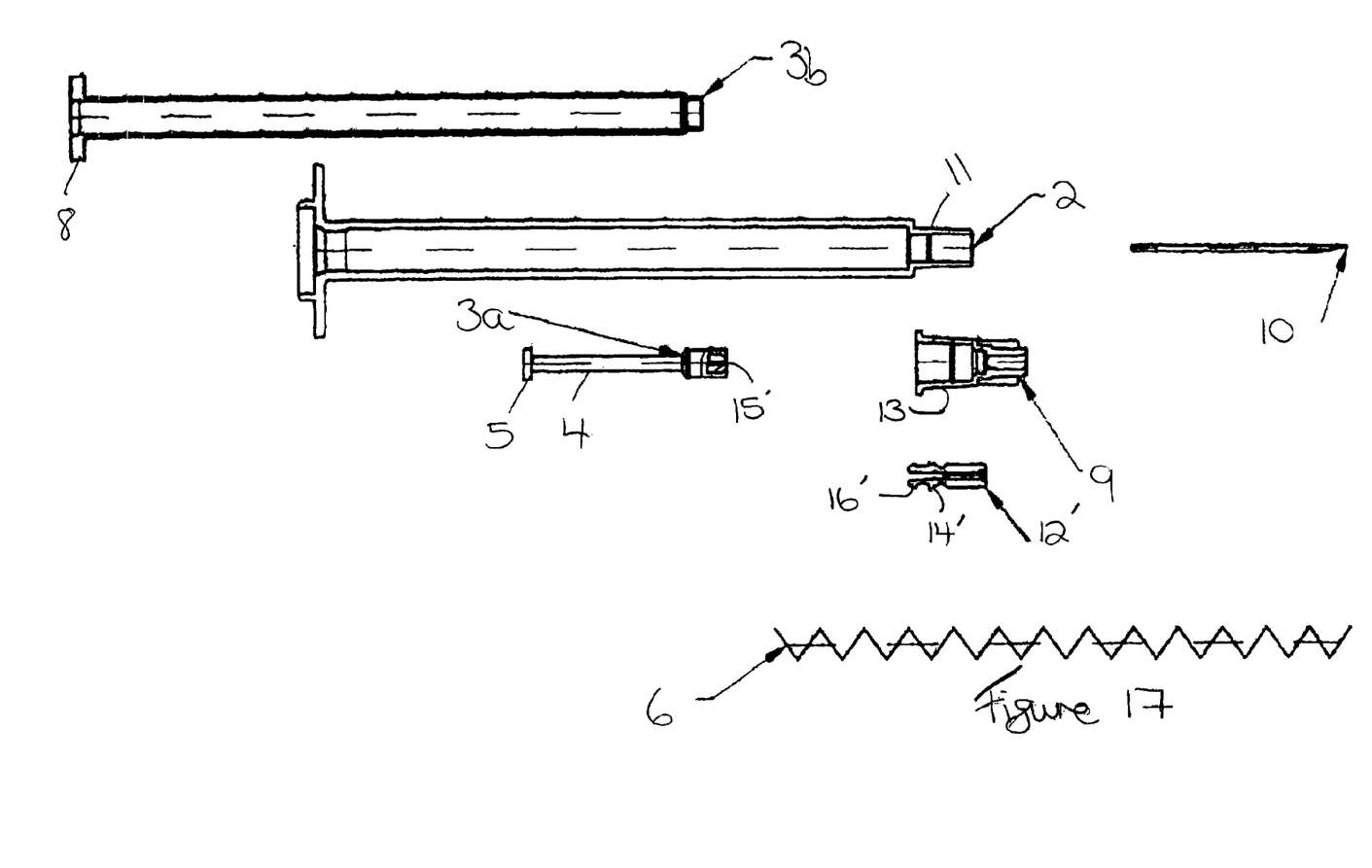
FIG. 17 shows an exploded side view of the syringe of FIGS. 12 to 16.

It can be seen from FIGS. 5 and 11 that the needle carrier 12 is drawn completely into the second part 3b of the plunger 3 within the barrel 2, so that the needle 10 does not protrude therefrom. As such, needlestick injuries can be avoided. In order to avoid removal of the needle carrier 12 from the barrel 2, the actuator 8 is received in a recess 19 at the proximal end of the barrel 2 at the end of its stroke. It can be seen from FIG. 5 that access to the actuator 8 is restricted as a result, so that it is not possible to withdraw the plunger 3 from the barrel 2, which further improves the safety of the device.

A second embodiment of the invention is shown in FIGS. 12 to 17, which are described using the same reference numerals except where the features differ from those of the embodiment described above.

The second embodiment of the invention has carrier engagement means $16^1$ on the needle carrier $12^1$ which are in the form of resilient projections. The resilient projections $16^1$ have curved ends and are engageable with corresponding plunger engagement means $15^1$ in the form of a receptacle on the first part 3a of the plunger 3. Rounded feet 20 bound the opening of the receptacle $15^1$.

The needle carrier $12^1$ has retaining means $14^1$ in the form of a tapered wall on the needle carrier $12^1$ which permits movement of the needle carrier $12^1$ in one direction only, i.e. in the direction opposite to the actuation direction of the plunger 3. The tapered wall $14^1$ is adapted to rest against an undercut 21 inside the barrel 2. Movement of the needle carrier $12^1$ beyond the undercut 21 in the direction of actuation of the plunger 3 is not possible because the tapered wall $14^1$ is prevented from moving past the undercut 21. However, the taper of the tapered wall $14^1$ is such that the needle carrier $12^1$ can pass the undercut 21 when the needle carrier $12^1$ is moved in the opposite direction.

The operation of the second embodiment of the invention is similar to that of the first embodiment. Once the plunger 3 has expelled the substance to be injected through the needle 10, a force continues to be applied to the actuator 8 on the plunger 3 so that the plunger 3 moves further along the barrel 2 to engage the needle carrier $12^1$, as described in relation to the first embodiment above.

When the receptacle $15^1$ meets the resilient projections $16^1$, the rounded feet 20 that bound the receptacle $15^1$ move along the curved ends of the resilient projections $16^1$ in the manner of a cam to enclose the projections $16^1$. Once the resilient projections $16^1$ are within the receptacle $15^1$, they expand somewhat due to their resilience and are thus locked in the receptacle $15^1$.

The projections 18 on the second part 3b of the plunger 3 then move out of the recess 17 on the first part 3a, so that the first part 3a and second part 3b are unlocked from one another. This unlocking releases the spring, which expands, and the first part 3a, together with the needle carrier $12^1$, to which it is attached, moves under the restoring force of the spring in the direction opposite to the actuation direction of the plunger 3.

The syringe 1 of both of the embodiments described above is relatively easy to assemble, in that the spring can simply be dropped into the second part 3b of the plunger 3 and the elongate tubular member 4 of the first part 3a of the plunger 3 can be simply inserted into the spring 6, so that the head 5 on the elongate tubular member 4 rests against the spring 6 and retains it in the second part 3b of the plunger. Compression of the spring 6 is achieved by forcing the first part 3a into the second part 3b of the plunger 3, or vice versa, so that the first 3a and second 3b parts lock together by the projections 18 on the second part 3b locking into the corresponding recess 17 on the first part 3a, so that the spring 6 is retained in a compressed state.

The plunger 3, barrel 2 and needle hub 9 are all made of the same material. Suitable materials include medical grade polypropylene, polycarbonate and acetalic resin, such as "Hostaform"®.

The seal 7 is made of any suitable material, such as latex free plastic rubber. The needle 10 is made of stainless steel, or any other suitable material, and the spring 6 can be made of rubber, plastics or any suitable metal, such as passivated stainless steel.

It will be appreciated by a person skilled in the art that a number of modifications can be made to the embodiments described above. For example, it can be seen from FIGS. 12 to 16, that the resilient projections $15^1$ protrude beyond the end of the outer part 13 of the needle hub 9. It would be possible to enclose the projections 16¹ entirely within the outer part 13 of the needle hub 9, which would avoid interference of the resilient projections 16¹ with the substance to be injected, for example, by creating air bubbles in the substance, and would also help to avoid damage to the resilient projections 16¹ in the process of attaching the needle hub 9 to the barrel 2, or before that stage when the needle hub 9 is not in use.

Rather than the ball 15 being deformable so that it can engage the socket 16 in the first embodiment of the invention, the socket 16 could be cut out of a resilient material so that it could deform to receive the ball 15. The location of the ball 15 and socket 16 could also be reversed in that the socket 16 could be arranged in the first part 3a of the plunger 3 and the ball 15 in the needle carrier 12.

Similarly, in the second embodiment of the invention, the receptacle 15¹ could be located in the needle carrier 12¹ and the resilient projections 16¹ could be located on the first part 3a of the plunger 3. The receptacle 15¹ could be formed of a resilient material as an alternative to or in addition to the projections 16¹ being resilient.

The plunger engagement means 15 do not have to be integral with the first part 3a of the plunger and could be formed as a separate component. Similarly, the carrier engagement means 16 do not have to be integral with the needle carrier 12.

The second locking means 18 on the second part 3b of the plunger 3 in both described embodiments could be in the form of a recess and the first locking means 17 on the first part 3a of the plunger 3 could be in the form of projections.

The first 17 and second 18 locking means do not have to be integral with the first 3a and second 3b parts of the plunger, respectively, and could be formed as separate parts.

Similarly, the head 5 on the elongate tubular member 4 of the first part 3a of the plunger does not have to be integral therewith, but could be a separate component.

Although the needle 10 is described above as being bonded to the needle carrier 12, the needle 10 could simply be retained in the needle carrier 12 by means of a close fit.

The spring 6 could be replaced by any other resilient member, such as a tube made of a resilient material.

The invention claimed is:

1. A syringe comprising:
    a barrel for containing a substance to be injected, the barrel comprising a collar at a distal end of the barrel;
    a needle carrier for carrying a needle fitted within a needle hub comprising an outer part which is a close fit around the outside of the collar such that the needle carrier projects into the collar, and
    a plunger which is adapted to be movable in the barrel to expel the substance to be injected from the needle,
    the plunger having a first part contained within a second part and a resilient member comprising a spring therebetween, the first and second parts being adapted to be releasably locked together by a push fit to hold said spring in a compressed state,
    wherein in use, the first part of the plunger and the needle carrier are adapted to engage one another following expulsion of the substance, and the second part of the plunger is adapted to be unlocked from the first part following said engagement by releasing the push fit holding, allowing said spring to expand to propel the needle carrier into the barrel, wherein the needle carrier is released from the inside of the collar under a restoring force of said spring in a direction opposite to the actuation direction of the plunger, and release of the needle carrier from the collar comprises only linear movement in said direction.

2. A syringe as claimed in claim 1, wherein the needle hub outer part has a luer taper.

3. A syringe as claimed in claim 1, wherein the barrel comprises retaining means which retains the needle carrier, and wherein, in use, the retaining means is adapted to be forced away from the needle carrier after the unlocking of the first and second parts of the plunger to allow the release of the needle carrier from the outer part of the needle hub.

4. A syringe as claimed in claim 1, wherein the first part of the plunger is adapted to engage the needle carrier by way of engagement means.

5. A syringe as claimed in claim 4, wherein the engagement means comprise a resilient prong on the needle carrier and a receptacle on the first part of the plunger.

6. A syringe as claimed in claim 5, wherein the resilient prong on the needle carrier is located entirely within a needle hub that is attachable to the barrel of the syringe.

7. A syringe as claimed in claim 4, wherein the engagement means comprise a socket in the needle carrier and a corresponding ball on the first part of the plunger.

8. A syringe as claimed in claim 1, wherein the first and second parts of the plunger are adapted to be releasably locked together by way of locking means.

9. A syringe as claimed in claim 8, wherein the locking means comprise a protrusion on the second part of the plunger that is adapted to engage a corresponding recess on the first part.

10. A syringe as claimed in claim 1, wherein the plunger is adapted to be irremovably contained in the barrel following retraction of the needle carrier.

11. A syringe as claimed in claim 1, wherein the needle carrier is adapted to be removed from the syringe prior to expulsion of the substance.

12. A syringe as claimed in claim 1, wherein retaining means are provided to prevent axial movement of the needle carrier in the syringe during expulsion of the substance.

13. A syringe as claimed in claim 12, wherein the retaining means is a resilient catch that is adapted to grip the needle carrier when it is positioned for expulsion of the substance.

* * * * *

UNITED STATES PATENT AND TRADEMARK OFFICE
CERTIFICATE OF CORRECTION

PATENT NO. : 8,382,710 B2
APPLICATION NO. : 11/663015
DATED : February 26, 2013
INVENTOR(S) : Filippo Filippi It is certified that error appears in the above-identified patent and that said Letters Patent is hereby corrected as shown below:

On the Title Page, in Item [73], under Assignee, please delete "Sperian" and insert --Speriam--.

Signed and Sealed this
Twenty-third Day of July, 2013

Teresa Stanek Rea
*Acting Director of the United States Patent and Trademark Office*